United States Patent [19]

Dygos et al.

[11] Patent Number: 5,104,990
[45] Date of Patent: Apr. 14, 1992

[54] PROCESS FOR THE PREPARATION OF 3-ARYL-3-AMINOALKYL-2,6-DIOXOHEXAHYDROPYRIDINES

[75] Inventors: John H. Dygos, Northbrook; Kathleen T. McLaughlin, Arlington Heights; John S. Ng, Chicago; Kalidas Paul, Skokie, all of Ill.

[73] Assignee: G. D. Searle & Co., Chicago, Ill.

[21] Appl. No.: 486,027

[22] Filed: Feb. 27, 1990

[51] Int. Cl.$^5$ ............................................. C07D 211/40
[52] U.S. Cl. ..................................................... 546/219
[58] Field of Search ................................. 546/216, 219

[56] References Cited

U.S. PATENT DOCUMENTS 2,664,424 12/1953 Hoffmann et al. ................... 548/219
3,963,729  6/1976 Gittos et al. ........................ 514/328
4,461,771  7/1984 Gittos et al. ........................ 514/328
4,738,973  4/1988 Gittos et al. ........................ 514/328

FOREIGN PATENT DOCUMENTS 160273 12/1954 Australia .............................. 546/219

Primary Examiner—C. Warren Ivy
Assistant Examiner—Raymond Covington
Attorney, Agent, or Firm—J. Timothy Keane; Charles E. Smith; Paul D. Matukaitis

[57] ABSTRACT

Disclosed is a process for the preparation of 3-aryl-3-aminoalkyl-2,6-dioxohexahydropridines and particularly the compounds 3-[3-(dimethylamino)propyl]-3-(3-methoxyphenyl)-4, 4-dimethyl-2,6-piperidinedione, monohydrochloride, which is useful as an antidepressant.

the process of the present invention comprises the condensation of a sterically hindered nitrile with a sterically hindered α, β-unsaturated diester to produce a nitrile diester. These compounds can then undergo acid catalyzed cyclization and decarboalkoxylation in a one step process to provide the desired 3-aryl-3-aminoalkyl-2,6-dioxohexahydropyridine.

2 Claims, No Drawings

PROCESS FOR THE PREPARATION OF 3-ARYL-3-AMINOALKYL-2,6-DIOXOHEXAHYDROPYRIDINES

BACKGROUND OF THE INVENTION

The synthesis and utility of pharmacologically active pyridine derivatives and particularly the compound 3-[3-(dimethylamino)propyl]-3-(3-methoxyphenyl)-4,4-dimethyl-2,6-piperidinedione, monohydrochloride is described in U.S. Pat. No. 3,963,729, issued June 15, 1976. The compound is useful as an antidepressant. Methods for the preparation of such compounds are disclosed in the patent. In terms of the synthesis of compound 3-[3-(dimethylamino)propyl]-3-(3-methoxyphenyl)-4,4-dimethyl-2,6-piperidinedione, monohydrochloride, the procedure set forth in Scheme I is disclosed. U.S. Pat. No. 4,738,973 discloses use of the compound in treating anxiety and U.S. Pat. No. 4,461,771 discloses its use in treating migraine headaches.

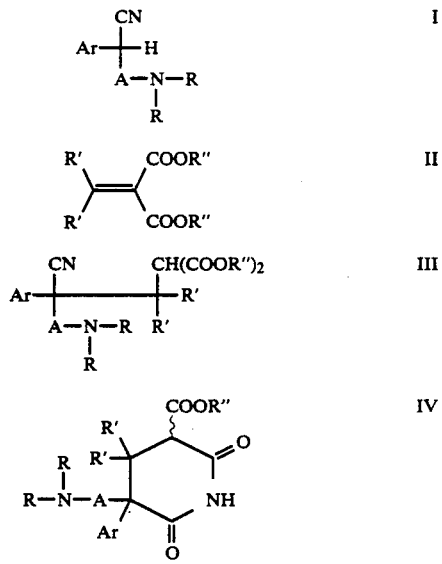

SCHEME I

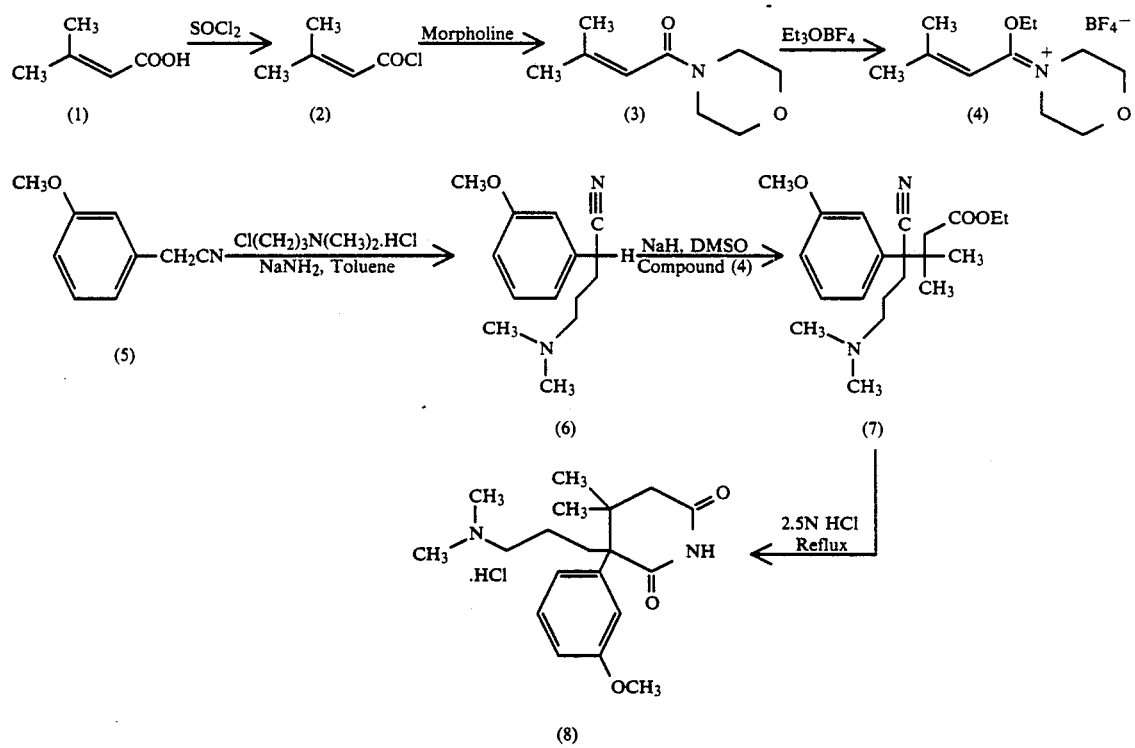

SUMMARY OF THE INVENTION

The process of the present invention comprises the condensation of a sterically hindered nitrile of the Formula I with a sterically hindered, $\alpha,\beta$-unsaturated diester of the Formula II to produce a nitrile diester of the Formula III. Compounds of the Formula III can undergo acid catalyzed cyclization to compounds of the Formula IV which can undergo decarboalkoxylation in a one step process to provide the desired 3-aryl-3-aminoalkyl-2,6-dioxohexahydropyridines of the Formulas V and VI.

DETAILED DESCRIPTION OF THE INVENTION

Disclosed is a method for the preparation of 3-aryl-3-aminoalkyl-2,6-dioxohexahydropyridines of the Formula V and their corresponding acid salts VI,

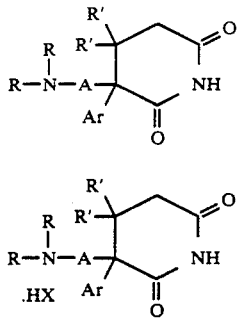

wherein A represents a straight or branched alkalene chain containing from 2 to about 6 carbon atoms, each R and R' are independently alkyl groups of from 1 to 10 carbon atoms and Ar is heterocyclic, unsubstituted aromatic or aromatic substituted with loweralkyl, loweralkoxy, halo, suitably protected amino, nitro, suitably protected hydroxy, or cyano. Preferred are aromatic ring systems or heterocylic ring systems of from 5 to about 10 carbon atoms such as phenyl, naphthyl, thiophenyl, imidazolyl, oxazolyl, pyrrolidino, piperidino, pyridino, morpholino or thiomorpholino. Preferred aromatic substituents include alkyl of from 1 to 10 carbon atoms, loweralkoxy of from 1 to 6 carbon atoms, chloro, fluoro, suitably protected amino or suitably protected hydroxy. Preferred acid salts (HX) are hydrochloric, sulfuric, phosphoric, methanesulfonic, p-toluenesulfonic and trifluoromethanesulfonic.

Preferred compounds to be made by the described process are those in which A is an alkalene chain of from 2 to 3 carbon atoms, R and R' are independently alkyl groups of from 1 to 4 carbon atoms and Ar is phenyl, thiophenyl or naphthyl substituted with alkyl of 1 to 4 carbon atoms, alkoxy of from 1 to 4 carbon atoms or chloro. The preferred acid salt is the hydrochloric acid salt.

The process of the present invention provides a number of advantages over the prior art (Scheme I), namely, a. the number of steps has been reduced from six to two or three with a concommitant three fold increase in the overall yield.

b. the imminium salt (4) in Scheme I has been eliminated as an intermediate in the synthesis thereby reducing the cost of preparation considerably by eliminating the expensive and hazardous reagent triethyloxonium tetrafluoroborate.

c. the hazardous sodium hydride/DMSO step has been eliminated.

d. the cost of raw materials and the process time for preparing large quantities of compounds of the Formula V and VI (e.g., 3-[3-(dimethylamino)-propyl]-3-(3-methoxyphenyl)-4,4-dimethyl-2,6-piperidinedione, monohydrochloride) have been significantly reduced.

The invention will be specifically described in terms of a preferred embodiment, the preparation of the 3-[3-(dimethylamino)propyl]-3-(3-methoxyphenyl)-4,4-dimethyl-2,6-piperidinedione, monohydrochloride.

The preferred process is summarized illustratively in the reaction Scheme II.

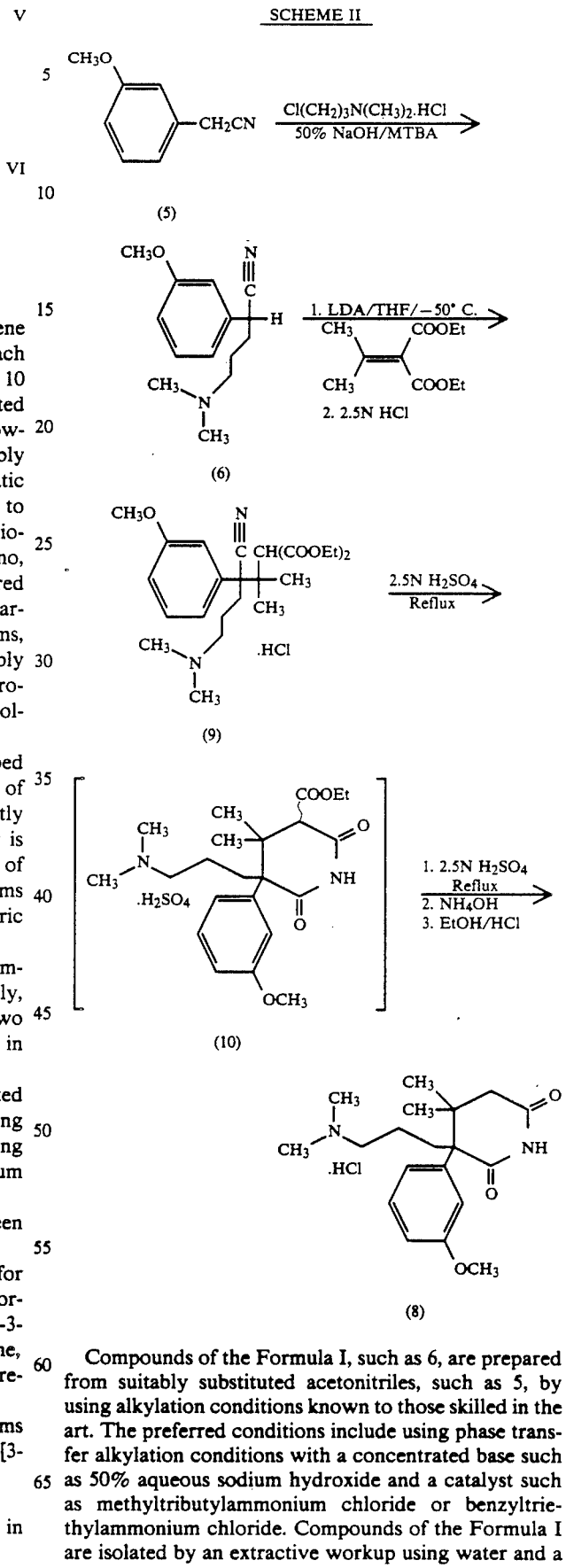

Compounds of the Formula I, such as 6, are prepared from suitably substituted acetonitriles, such as 5, by using alkylation conditions known to those skilled in the art. The preferred conditions include using phase transfer alkylation conditions with a concentrated base such as 50% aqueous sodium hydroxide and a catalyst such as methyltributylammonium chloride or benzyltriethylammonium chloride. Compounds of the Formula I are isolated by an extractive workup using water and a water-immiscible solvent, such as toluene. The product is partially purified by extraction into a dilute aqueous acid solution, such as hydrochloric acid. After the solution is washed with a water-immiscible solvent, such as toluene, it is treated with a base, such as sodium hydroxide, and the product is extracted into a water-immiscible solvent, such as toluene. The extract is dried by azeotropic distillation, and the solvent is removed by distillation. The crude product, such as 6, can be purified by distillation or can be used without further purification.

Compounds of the Formula III, such as 9, are prepared from compounds of the Formula I, such as 6, by the following general method. The compound of the Formula I, such as 6, is reacted with greater than 1 equivalent, preferably 1.1 equivalents, of a strong base, such as lithium diisopropylamide (LDA), and greater than 1 equivalent, preferably 1.1 equivalents, of a compound of the Formula II, such as diethyl 2-(1-methylethylidine)propanedioate, in an organic solvent, such as tetrahydrofuran, at $-100°$ to $0°$ C., preferably at $-50°$ C. Cosolvents, such as hexamethylphosphoric triamide (HMPT), 1,3-dimethyl-2-imidazolidinone (DMEU) or 1,3-dimethyl-3, 4,5,6-tetrahydro-2(1H)-pyrimidinone (DMPU), may also be added to the reaction. Alternatively, other solvents, such as ether, 1,2-dimethoxyethane or tert butyl methyl ether, may be used with or without cosolvents. For purposes of this application the term "strong base" refers to a substance sufficiently basic to abstract an $\alpha$-proton from compounds of the Formula I. Suitable strong bases include lithium diisopropylamide, lithium 2,2,6,6-tetramethylpiperidide, lithium bis(trimethylsilyl) amide, potassium bis(trimethylsilyl)amide, sodium bis(trimethylsilyl)amide, lithium cyclohexylisopropylamide, sodium amide, alkyllithiums such as methyllithium, n-butyllithium, sec-butyllithium and tert-butyllithium, and other strong bases known in the art.

Isolation of the resultant compounds of the Formula III, such as 9, involves quenching the cold reaction solution with an aqueous hydrochloric acid solution, and washing the mixture with a water-immiscible solvent, such as toluene, to remove neutral impurities such as unreacted diethyl 2-(1-methylethylidine)propanedioate. The product is then extracted as its hydrochloride salt into a water-immiscible solvent, such as methylene chloride or chloroform, leaving other basic reaction impurities in the aqueous acidic layer. The solvent is partially removed by distillation, and the product is crystallized by the addition of a suitable organic solvent, such as ethyl acetate or ethanol. The product can also be isolated by complete removal of the solvent by distillation, and used without any purification. Alternatively, the methylene chloride extraction may be omitted, and the product isolated by crystallization from the aqueous acidic layer. Other aqueous acids, such as sulfuric acid or phosphoric acid, may be used and the product isolated as the corresponding acid salt. The product can also be isolated as the free amine by quenching the cold reaction mixture with aqueous ammonium chloride, and extracting the product into an organic solvent such as toluene, ethyl acetate or methylene chloride; or, alternatively, by neutralization of the isolated hydrochloride salt with an aqueous solution of sodium bicarbonate, and extraction of the free base into an organic solvent, such as toluene, ethyl acetate or methylene chloride. The free base can be isolated by removal of the solvent by distillation.

Compounds of the Formula V or VI, such as 8, are prepared from compounds of the Formula III, such as 9, by heating the compound in aqueous acid at reflux until the reaction is complete. The compound of the Formula III may be the free amine or a pharmaceutically acceptable acid salt, such as the hydrochloric acid, sulfuric acid, phosphoric acid or organic acid salt. The preferred acid salts are the sulfuric acid andhydrochloric acid salts. The preferred acid concentration for preparing 8 is 1-3N sulfuric acid or 1-3N hydrochloric acid, but other concentrations, such as 0.5-12N, can be used. The reaction proceeds through a cyclized intermediate of the Formula IV, or its corresponding acid salt, such as 10, ethyl 5-[3-(dimethylamino)propyl]-5-(3-methoxyphenyl)-4,4-dimethyl-2,6-dioxo-3-piperidinecarboxylate sulfate, which can be isolated if desired. The preferred method, however, is to convert compounds of the Formula III, such as 9, to compounds of the Formula V or VI, such as 8, without isolation of the intermediate compound of the Formula IV.

In order to isolate the resultant compound of the Formula VI, such as 8, the reaction mixture is basified with a suitable base, such as ammonium hydroxide, preferably to pH 7.5-9.5, and the product is extracted into methylene chloride or chloroform as the free base. The solvent is removed by distillation, and the free base is dissolved in a hot alcohol solvent, such as methanol, ethanol, or isopropanol. The compound of the Formula VI, such as 8, is precipitated by the addition of 1.1 equivalents of concentrated hydrochloric acid to the hot alcohol solution before cooling. Alternatively, when the reaction is carried out in aqueous hydrochloric acid, the compound of the Formula VI, such as 8, can be isolated by crystallization from the aqueous reaction mixture. The compound of the Formula VI can be further purified by recrystallization from a suitable solvent, such as methanol, methanol/ethanol or aqueous ethanol. Other acids, such as sulfuric acid, phosphoric acid, methanesulfonic acid, p-toluenesulfonic acid or trifluoromethanesulfonic acid, may also be used to convert the free base to the corresponding compound of the Formula VI.

In order to isolate the compound of the Formula V, the reaction mixture is basified with a suitable base, such as ammonium hydroxide, preferably to pH 7.5-9.5, and the product is extracted into methylene chloride or chloroform as the free base. The solvent is removed by distillation, and the compound of the Formula V is isolated by recrystallization of the residue from an alcohol solvent, such as methanol, ethanol or isopropanol. Alternatively, the methylene chloride extraction may be omitted, and the compound of the Formula V isolated by crystallization from the basified aqueous layer. The compound of the Formula V may be further purified by recrystallization from an organic solvent, such as methanol, ethanol or isopropanol.

Compounds of the Formula V can be converted to compounds of the Formula VI by dissolution in a hot alcohol solvent followed by addition of the desired acid as described above.

Compounds of the Formula V and VI, such as 8, can also be prepared from compounds of the Formula IV, or the corresponding acid salt, such as 10, by heating the compound in aqueous acid at reflux and working the mixture up in the same manner as described above.

Compounds of the Formula V or VI, such as 8, can be prepared directly from compounds of the Formula I, such as 6, without isolation of the compounds of the Formula III, such as 9. The reaction of a compound of the Formula I, such as 6, with a suitable base, such as LDA, and a compound of the Formula II, such as diethyl 2-(1-methylethylidine)propanedioate, is carried out by the methods described above for the preparation of compounds of the Formula III. After the reaction mixture is treated with aqueous acid and an organic solvent, such as toluene, the aqueous acidic layer containing the compound of the Formula III, such as 9, is heated at reflux to afford the desired compound of the Formula VI, such as 8. The preferred acids are sulfuric acid and hydrochloric acid, but other acids, such as phosphoric acid or organic acids, can be used, and concentrations of 0.5-12N can be used. The product can be isolated as the compound of the Formula V or the Formula VI by the methods described above. Alternatively, the reaction mixture can be basified, the free base extracted into methylene chloride or chloroform, and the solvent removed by distillation. The compound of the Formula VI, such as 8, can be separated from basic reaction impurities by crystallization from aqueous hydrochloric acid. The isolated product of the Formula VI can be further purified as described above.

The practice of the present invention is further illustrated by the following illustrative examples which are not intended to be limiting.

EXAMPLE 1

Preparation of
α-[3-(dimethylamino)propyl]-3-methoxybenzene-acetonitrile (6)

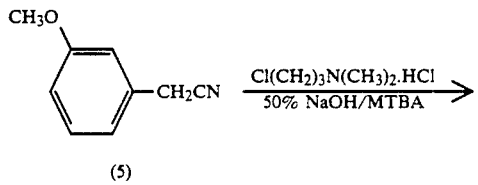

(5)

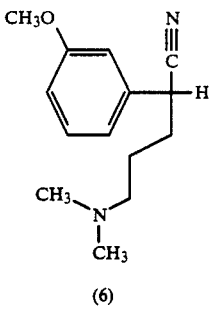

(6)

A reaction vessel is charged with 4.84 kg of 3-chloro-N,N-dimethylpropanamine, monohydrochloride, 4.94 kg of 3-methoxybenzeneacetonitrile (5), 110 g of methyltributylammonium chloride (75% w/w in water) and 13L of aqueous sodium hydroxide solution (50% w/w). The slurry is stirred at 40° C. for about 22 h. When the reaction is complete as indicated by gas chromatography, heating is discontinued. The reaction mixture is diluted with 20L of water and 20L of toluene and stirred for 15 min. After separation of the layers, the aqueous phase is extracted with 10L of toluene. The combined organic phase is extracted with a solution of 4.13L of aqueous hydrochloric acid (36% w/w) in 20L of water. The aqueous phase is washed with 10L of toluene, basified with 2.8L of aqueous sodium hydroxide solution (50% w/w) and extracted twice with a total of 30L of toluene. The combined organic phase is washed with 10L of water and filtered. The filtrate is dried by azeotropic distillation, and the solvent is removed by distillation under reduced pressure to give 6.58 kg (92% of theory based on 3-chloro-N,N-dimethylpropanamine, monohydrochloride; product contains toluene) of an oily residue which is α-[3-(dimethylamino)propyl]-3-methoxybenzeneacetonitrile (6).

EXAMPLE 2

Preparation of diethyl
2-[2-cyano-5-(dimethylamino)-2-(3-methoxyphenyl)-1,1-dimethylpentyl]propanedioate, monohydrochloride
(9)

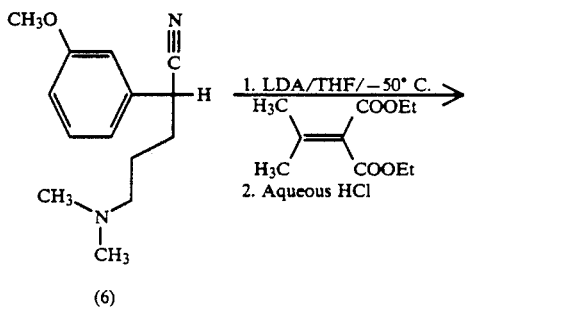

(6)

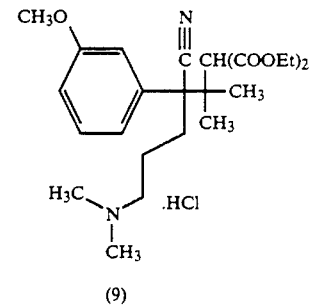

(9)

A nitrogen atmosphere is applied to a reaction vessel, and 36L of tetrahydrofuran is added. The solvent is cooled to less than −40° C. and 11.89 kg of lithium diisopropylamide in tetrahydrofuran/n-heptane (2.1M solution) is added. A solution of 6.58 kg of α-[3-(dimethylamino)propyl]-3-methoxybenzeneacetonitrile (6) in 10L of tetrahydrofuran is added at less than −20° C. A 5-L portion of tetrahydrofuran is used as a rinse, and the mixture is stirred at less than −20° C. for 30 min. The mixture is cooled to less than −50° C., and a solution of 6.25 kg of diethyl 2-(1-methylethylidine)-propanedioate in 10L of tetrahydrofuran is added to the reaction mixture at a rate such that the temperature does not exceed −50° C. A 5-L portion of tetrahydrofuran is used as a rinse, and the mixture is stirred at less than −50° C. for 30 min. The cold reaction mixture is added to a stirred solution of 24L of aqueous hydrochloric acid (36% w/w) in 90L of water cooled to less than 10° C., and a 15-L portion of tetrahydrofuran is used to rinse the reactor. The mixture is extracted twice with 20-L portions of toluene, and the toluene phase is back-extracted with a solution of 2L of aqueous hydrochloric acid (36% w/w) in 8L of water. The aqueous acidic extract is combined with the aqueous acidic phase from above and extracted twice with 40-L portions of methylene chloride. The combined methylene chloride extracts are washed with a solution of 2L of aqueous hydrochloric acid (36% w/w) in 8L of water, and the layers are separated. The methylene chloride phase is filtered and concentrated to low volume by distillation at atmospheric pressure. A 70-L portion of ethyl acetate is added, and the resulting slurry is cooled to less than 10° C. The resulting solid is collected by filtration and washed with 30L of ethyl acetate. The solid is dried at 50° C. to give 11.24 kg (84.6% of theory) of diethyl 2-[2-cyano-5-(dimethylamino)-2-(3-methoxyphenyl)-1,1-dimethylpentyl]propanedioate, monohydrochloride (9).

EXAMPLE 3

Preparation of 3-[3-(dimethylamino)propyl]-3-(3-methoxyphenyl)-4,4-dimethyl-2,6-piperidinedione, monohydrochloride (8)

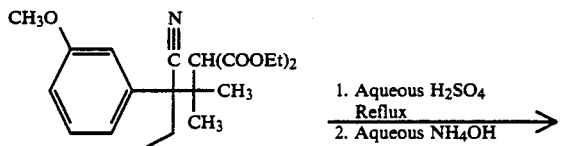

(9)

1. Aqueous H$_2$SO$_4$ Reflux
2. Aqueous NH$_4$OH
3. EtOH/Aqueous HCl

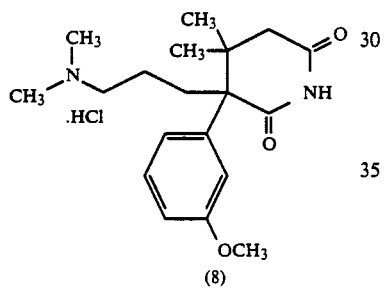

(8)

A reaction vessel is charged with 11.24 kg of diethyl 2-[2-cyano-5-(dimethylamino)-2-(3-methoxyphenyl)-1,1-dimethylpentyl]propanedioate, monohydrochloride (9), and a solution of 11.46 kg of sulfuric acid (96% w/w) in 90L of water is added. The reaction mixture is refluxed for about 54 h. When the reaction is complete as indicated by thin layer chromatography, the solution is cooled to 25° C. The aqueous solution is washed with 20L of methylene chloride. The aqueous phase is mixed with 40L of methylene chloride and basified with 19L of aqueous ammonium hydroxide (29% w/w) while maintaining the temperature at less than 30° C. After separation of the layers, the aqueous phase is extracted twice with 20-L portions of methylene chloride. The combined organic phase is washed twice with 20-L portions of water and filtered through a layer of diatomaceous earth.

The filtrate is concentrated to low volume by distillation at atmospheric pressure and diluted with 40L of ethanol. The mixture is concentrated by distillation at atmospheric pressure until the temperature reaches 75° C. An additional 10-L portion of ethanol is added, and the mixture is refluxed until the solids have dissolved. A 2.6-kg portion of aqueous hydrochloric acid (36% w/w) is added to the hot solution at a rate that maintains a gentle reflux. The mixture is allowed to cool to 25° C., and the resulting slurry is cooled to less than 10° C. The solid is collected by filtration and washed with 20L of ethanol. The solid is reslurried in 20L of ethanol, filtered and washed with 20L of ethanol. The product is dried at 50° C. to give 7.38 kg (83.5% of theory) of 3-[3-(dimethylamino)propyl]-3-(3-methoxyphenyl)-4,4-dimethyl-2,6-piperidinedione, monohydrochloride (8).

EXAMPLE 4

A. Preparation of 3-[3-(dimethylamino)propyl]-3-(3-methoxyphenyl)-4,4-dimethyl-2,6-piperidinedione, monohydrochloride (8) from α-[3-(dimethylamino)propyl]-3-methoxybenzeneacetonitrile (6)

A 1-g sample of α-[3-(dimethylamino)propyl]-3-methoxybenzene-acetonitrile (6) is reacted with 0.95 g of diethyl 2-(1-methylethylidine)propanedioate by the method described in Example 2. The cold reaction mixture is added to a solution of 1.35 ml of sulfuric acid in 13 ml of water instead of aqueous hydrochloric acid, and the aqueous mixture is extracted twice with toluene. The methylene chloride extractions and the subsequent isolation of product are eliminated. The aqueous sulfuric acid mixture is refluxed until reaction is complete and extractions of products are performed as described in Example 3. The title compound was isolated from 2N aqueous hydrochloric acid instead of from ethanol/hydrochloric acid.

EXAMPLE 5

B. Preparation of 3-[3-(dimethylamino)propyl]-3-(3-methoxyphenyl)-4,4-dimethyl-2,6-piperidinedione, monohydrochloride (8) from ethyl 5-[3-(dimethylamino) propyl]-5-(3-methoxyphenyl)-4,4-dimethyl-2,6-dioxo-3-piperidinecarboxylate, monohydrochloride The title compound is prepared by the method of Example 3 using 2 g of ethyl 5-[3-(dimethylamino)propyl]-5-(3-methoxyphenyl)-4,4-dimethyl-2,6-dioxo-3-piperidinecarboxylate, monohydrochloride instead of using the title product of Example 2 as the starting material.

EXAMPLE 6

Preparation of 3-[3-dimethylamino)propyl]-3-(3-methoxyphenyl)-4,4-dimethyl-2,6-piperidinedione The title compound is prepared from 10.7 g of diethyl 2-[2-cyano-5-(dimethylamino)-2-(3-methoxyphenyl)-1,1-dimethylpentyl]propanedioate, monohydrochloride (9) by the method described in Example 3. Methylene chloride is eliminated from the reaction mixture during the basification with ammonium hydroxide (29%), and the resulting slurry is cooled and filtered to afford the title compound. Dissolution in ethanol and treatment with hydrochloric acid are also eliminated from the work-up.

EXAMPLE 7

Preparation of diethyl 2-[2-cyano-5-(dimethylamino)-2-(3-methoxyphenyl)-1,1-dimethylpentyl]propanedioate (free base of (9))

The title compound is prepared by the method of Example 2 from 5 g of α-[3-(dimethylamino) propyl]-3-methoxybenzeneacetonitrile (6), using 20 ml of DMPU as cosolvent. After concentration of the methylene chloride phase, the residue is partitioned between a solution of 0.5 g of sodium bicarbonate in 10 ml of water and 10 ml of toluene. The aqueous phase is further extracted with toluene, and the combined organic layers are washed with water The organic phase is concentrated in vacuo to dryness to give the title compound, which is used in subsequent reactions without further purification.

EXAMPLE 8

Preparation of 3-[3-di(methylamino)propyl]-3-(3-methoxyphenyl)-4,4-dimethyl-2,6-piperidinedione, monohydrochloride (8) from diethyl 2-[2-cyano-5-(dimethylamino)-2-(3-methoxyphenyl)-1,1-dimethylpentyl]propanedioate The title compound is prepared from 5 g of diethyl 2-[2-cyano-5-(dimethylamino)-2-(3-methoxyphenyl)-1,1-dimethylpentyl]propanedioate by the method of Example 7. A 2.5N hydrochloric acid solution is used for the reaction instead of 2-2.5N sulfuric acid, and the free base of the title compound is isolated. The free base is recrystallized from aqueous methanol. The free base is dissolved in ethanol, hydrochloric acid (36% w/w) is added, and the mixture is cooled and filtered to afford the title compound.

EXAMPLE 9

Preparation of 3-[3-(dimethylamino)propyl]-3-(3-methoxyphenyl)-4,4-dimethyl-2,6-piperidinedione, monohydrochloride (8) using 96% sulfuric acid The title compound is prepared from 1 g of diethyl 2-[2-cyano-5-(dimethylamino)-2-(3-methoxyphenyl)-1,1-dimethylpentyl]propanedioate, monohydrochloride (9) by the method of Example 3 using 1.65 ml of sulfuric acid (96% w/w) in 3.35 ml of water instead of the more dilute solution. The reflux time was decreased to 12h.

EXAMPLE 10

Preparation of 3-[3-(dimethylamino)propyl]-3-(3-methoxyphenyl)-4,4-dimethyl-2,6-piperidinedione, monohydrochloride (8) using 1N hydrochloric acid The title compound was prepared by the method of Example 3 using 1 g of diethyl 2-[2-cyano-5-(dimethylamino)-2-(3-methoxyphenyl)-1,1-dimethylpentyl]-propanedioate, monohydrochloride (9) in 10 ml of 1N hydrochloric acid instead of 2-2.5N sulfuric acid.

EXAMPLE 11

Preparation of diethyl 2-[2-cyano-5-(dimethylamino)-2-(3-methoxyphenyl)-1,1-dimethylpentyl]propanedioate, monohydrochloride (9)

The title compound was prepared from 1 g of α-[3-(dimethylamino)propyl]-3-methoxybenzeneacetonitrile (6) by the method of Example 2. The reaction temperature was maintained entirely at about −20° C. instead of cooling to less than −50° C. before the addition of diethyl 2-(1-methylethylidine)propanedioate. A 1.4-g sample (70% of theory) of the title compound was isolated.

Although the foregoing invention has been described in some detail by way of illustration and example for purposes of clarity of understanding; one skilled in the art can readily envision various modifications and changes which are nevertheless within the scope of the invention. Therefore, it is desired that the process of this invention be limited only by the scope of the appended claims.

What is claimed is:

1. A method for the preparation of 3-[3-(dimethylamino)propyl]-3-(3-methoxyphenyl)-4,4-dimethyl-2,6-piperidinedione, said method comprising:

refluxing diethyl 2-[2-cyano-5-(dimethylamino)-2-(3-methoxyphenyl)-1,1-dimethylpenyl]propanedioate in acid having a concentration in a range from about 0.5N to about 12N for a time and at a temperature sufficient to produce ethyl5-[3-(dimethylamino)propyl]-5-(3-methoxyphenyl)-4,4-dimethyl-2,6-dioxo-3-piperidinecarboxylate intermediate and, further, refluxing said intermediate in acid having a concentration in a range from about 0.5N to about 12N for a time and at a temperature sufficient to produce 3-[3-(dimethylamino)propyl]-3(3-methoxypheynyl)-4,4-dimethyl-2,6-piperidinedione.

2. A method for the preparation of 3-[(3-(dimethylamino)propyl]-3-(3-methoxyphenyl)-4,4-dimethyl-2,6-piperidinedione, which method comprises:

refluxing ethyl 5-[3-(dimethylamino)propyl]-5-(3-methoxyphenyl)-4,4-dimethyl-2,6-dioxo-3-piperidinecarboxylate in acid having a concentration in a range from about 0.5N to about 12N for a time and at a temperature sufficient to produce 3-[3-(dimethylamino)propyl]-3-(methoxyphenyl)-4,4-dimethyl-2,6-piperidinedione.

* * * * *